(12) United States Patent
Yamakawa et al.

(10) Patent No.: US 10,316,350 B2
(45) Date of Patent: Jun. 11, 2019

(54) PRETREATMENT METHOD AND NUCLEIC-ACID-EXTRACTING KIT USABLE FOR THE SAME

(71) Applicant: MIZUHO MEDY CO., LTD., Saga (JP)

(72) Inventors: Kazutomi Yamakawa, Saga (JP); Takashi Nagano, Saga (JP)

(73) Assignee: MIZUHO MEDY CO., LTD., Saga (JP)

(*) Notice: Subject to any disclaimer, the term of this patent is extended or adjusted under 35 U.S.C. 154(b) by 0 days.

(21) Appl. No.: 15/505,329

(22) PCT Filed: Sep. 2, 2015

(86) PCT No.: PCT/JP2015/074927
§ 371 (c)(1),
(2) Date: Feb. 21, 2017

(87) PCT Pub. No.: WO2016/035812
PCT Pub. Date: Mar. 10, 2016

(65) Prior Publication Data
US 2017/0335370 A1    Nov. 23, 2017

(30) Foreign Application Priority Data
Sep. 3, 2014  (JP) ................................ 2014-179111

(51) Int. Cl.
*C12Q 1/68* (2018.01)
*C12Q 1/6806* (2018.01)
(Continued)

(52) U.S. Cl.
CPC .......... *C12Q 1/6806* (2013.01); *C12N 15/09* (2013.01); *C12N 15/1006* (2013.01); *C12N 15/1017* (2013.01)

(58) Field of Classification Search
None
See application file for complete search history.

(56) References Cited

U.S. PATENT DOCUMENTS

| 5,916,775 A | 6/1999 | Hayashizaki |
| 2004/0014070 A1 | 1/2004 | Pinsl-Ober et al. |

(Continued)

FOREIGN PATENT DOCUMENTS

| EP | 0 389 063 | 9/1990 |
| EP | 0 819 696 | 1/1998 |

(Continued)

OTHER PUBLICATIONS

Tian et al. (Analytical Biochem, 2000, 283, 175-191).*

(Continued)

*Primary Examiner* — Stephanie K Mummert
(74) *Attorney, Agent, or Firm* — Wenderoth, Lind & Ponack, L.L.P.

(57) ABSTRACT

The present invention provides a method capable of realizing pretreatment process of genetic screening according to a POCT mode. The method includes: making a sample, extraction liquid for extracting nucleic-acid contained in the sample, silica particles, and a filtering material contact with each other; making the filtering material carry composite material of the nucleic-acid and the silica particles thereon; and then delivering the filtering material to a nucleic-acid-amplifying process by means of reaction solution for amplifying nucleic-acid, wherein particle diameters of the silica particles and concentration of the silica particles in the reaction solution for amplifying nucleic-acid are set up within a predetermined range.

10 Claims, 7 Drawing Sheets

Specification includes a Sequence Listing.

(51) Int. Cl.
*C12N 15/09* (2006.01)
*C12N 15/10* (2006.01)

(56) References Cited

U.S. PATENT DOCUMENTS

| | | |
|---|---|---|
| 2006/0257907 A1 | 11/2006 | Wheeler et al. |
| 2008/0132694 A1 | 6/2008 | Himmelreich et al. |
| 2011/0027874 A1 | 2/2011 | Wheeler et al. |
| 2011/0091873 A1 | 4/2011 | Nasarabadi |
| 2011/0251382 A1 | 10/2011 | Deggerdal et al. |

FOREIGN PATENT DOCUMENTS

| | | |
|---|---|---|
| JP | 2680462 | 8/1997 |
| JP | 10-155481 | 6/1998 |
| JP | 11-92494 | 4/1999 |
| JP | 11-146783 | 6/1999 |
| JP | 2004-201607 | 7/2004 |
| JP | 2005-514036 | 5/2005 |
| JP | 2005-253464 | 9/2005 |
| JP | 3812696 | 6/2006 |
| JP | 10-72485 | 3/2010 |
| JP | 2014-30364 | 2/2014 |
| WO | 2005/021748 | 3/2005 |
| WO | 2006/113359 | 10/2006 |

OTHER PUBLICATIONS

Kim et al. (Analyst, 2010, 135, p. 2408-2414).*
Makowski et al. (Nucleic Acids Research, 1995, 13(18):3788-3789) (Year: 1995).*
R. Boom et al., "Rapid and Simple Method for Purification of Nucleic Acids", Journal of Clinical Microbiology, vol. 28, (1990) pp. 495-503.
B. Vogelstein and D. Gillespie, "Preparative and analytical purification of DNA from agarose", PNAS, vol. 76(2), (1979) pp. 615-619.
Written Opinion of the International Searching Authority dated Dec. 1, 2015 in corresponding International Application No. PCT/JP2015/074927 (with English translation).
International Search Report dated Dec. 1, 2015 in corresponding Application No. PCT/JP2015/074927.
Extended European Search Report dated Jan. 16, 2018 in corresponding European patent application No. 15837848.
Office Action issued by Intellectual Property Office of Singapore (IPOS) dated Mar. 5, 2018 in corresponding Singaporean Patent Application No. 11201701732Y.
Search Report issued by Intellectual Property Office of Singapore (IPOS) dated Mar. 5, 2018 (completed Feb. 23, 2018) in corresponding Singaporean Patent Application No. 11201701732Y.
David Moore et al., "Purification and Concentration of DNA from Aqueous Solutions", Current Protocols in Molecular Biology, 2002, Supplemental 59, pp. 2.2.1-2.1.10.
Office Action dated Dec. 19, 2017 in corresponding Korean Patent Application No. 10-2017-7004470, with English translation.
Office Action by the Canadian Intellectual Property Office (CIPO) dated Sep. 25, 2018 in corresponding Canadian Patent Application No. 2,957,776.
Tian et al., "Evaluation of Silica Resins for Direct and Efficient Extraction of DNA from Complex Biological Matrices in a Miniaturized Format", Analytical Biochemistry, 2000, vol. 283, pp. 175-191.

* cited by examiner

PRETREATMENT METHOD AND NUCLEIC-ACID-EXTRACTING KIT USABLE FOR THE SAME

BACKGROUND OF THE INVENTION

1. Field of the Invention

The present invention relates to a pretreatment method of, prior to a nucleic-acid-amplifying process, extracting nucleic-acid by means of a solid-phase extraction method.

Herein, the nucleic-acid-amplifying process is performed in order to detect and/or identify the base sequence of target nucleic-acid.

More particularly, the present invention is capable of realizing processes according to a POCT mode without any special physical and chemical instruments.

The word of "POCT" stands for "Point of Care Testing", and means an inspection performed near a subject and/or by the subject himself/herself.

The Japan society for clinical laboratory automation has defined, in POCT guidelines thereof, that the POCT is "an inspection for contributing to improvement in items including: prompt and appropriate medical treatment and nursing; prevention of disease; quality of medical cares, such as health care administration; QOL (Quality of life); and satisfaction of the cares."

2. Description of the Related Art

In recent years, the life science field has remarkably developed, and nucleic-acid (such as DNA and RNA)-analyzing techniques have been widely used.

The nucleic-acid-analyzing techniques have been used widely, for example, in: biological fields (species identification, studies of the origins thereof, or the like.); medical fields (diagnosis of diseases, or the like.); and other fields close to daily life (confirmation of the food safety, or the like.).

Target nucleic-acid may include, for example, specific gene sequences of foreign genes that do not exist in an owner of the sample and other specific base sequences. "Genetic screening" is a technique that amplifies and analyzes the target nucleic-acid by means of a PCR method and/or an isothermal nucleic-acid-amplifying method among nucleic-acid-analyzing techniques.

Whereas, culture tests and immunological examinations of inspections by means of antigens and/or antibodies belong to conventional infectious disease diagnostic techniques.

In disease diagnosis in the medical fields, particularly in early infectious disease diagnosis, the genetic screening has higher sensitivity than the conventional infectious disease diagnostic techniques, or the like.

Utilizing the genetic screening enables to detect and/or identify almost all pathogenic microorganisms including: bacteria; fungi; protozoa; and viruses, which may be responsive for causing infectious diseases in human beings.

Accordingly, the genetic screening is considered to be a useful inspection method for early diagnosis of the infectious diseases, and has been frequently used in facilities with exclusive inspecting rooms and/or laboratories, such huge hospitals (e.g. base hospitals), health laboratories, research establishments (e.g. universities and companies), other institutions with many staffs, or the like.

In "2012-Clinical-examination-market No. 3/bacteria/gene/POC/biopsy", the Fuji Keizai Co., LTD. has pointed out "It is expected that the market of the genetic screening will expand at an annual ratio of 2 through 3% also after 2013." It is expected that the market of the genetic screening will increase the importance thereof with respect to not only the early diagnosis of the infectious diseases but also economic activities.

The genetic screening is, however, hardly used in small medical facilities often visited by ordinary people (e.g. private hospitals and/or clinics in the town).

The reason why is as follows.

Firstly, the genetic screening requires complicated and time-consuming operation before performing the same, such as reagent preparation, nucleic-acid extraction, or the like, which forces a heavy burden on the small medical facilities.

Secondly, performing the genetic screening also requires physical and chemical equipment and automation equipment. The physical and chemical equipment includes a centrifugal machine and a micro pipette for extracting nucleic-acid. Thereby, both initial investment costs and maintenance costs must be higher.

Thirdly, it cannot be said that doctors, nurses, or the like in the small medical facilities are fully conversant with the genetic screening.

Meanwhile, testing kits not related to the genetic screening but corresponding to the POCT (for example, kits according to an labeled antibody method, an immunoturbidimetric method, a latex agglutination method, a immunochromatography method, or the like.) are widely used also in the small medical facilities.

According to the summary announced by the Japan Ministry of Health, Labor and Welfare in December 2009, actual shipped production of rapid examination kits against influenza antigen in the previous season have reached about 13 million tests.

The genetic screening using target nucleic-acid has more sensitivity than an immunological examination, and is very effective in rapid diagnosis of early infectious disease.

Unfortunately, neither a POCT kit applicable for the genetic screening nor another kit pursuant the same exists at present.

For this reason, in the small medical facilities, the genetic screening cannot be performed. Alternatively, specimens are collected to be left for inspection by one of external facilities. Therefore, genetic screening results cannot be obtained quickly.

If POCT kits applicable for the genetic screening and a method for the same have been developed, also in the small medical facilities, the genetic screening can be performed, thereby obtaining extremely high utility.

Herein, the present genetic screening method can be roughly divided into the following three processes.

A first process (pretreatment) performs: after having collected a specimen, exposing nucleic-acid conjugated by shells and/or membrane of protein in the specimen therefrom; and washing and separating contaminants, such as protein, by means of organic solvent, a solid-phase carrier, or the like to isolate the nucleic-acid only.

A second process (amplification of the target nucleic-acid) performs: utilizing a template of the separated nucleic-acid; and amplifying the target nucleic-acid according to a nucleic-acid amplification reaction method, such as PCR, LAMP reaction, or the like.

A third process (detection and analysis) performs: during and/or after the amplification reaction, using the amplified target nucleic-acid and/or markers conjugating to the same to carry out a qualitative step and/or a quantitative step related thereto.

There is automating equipment for easily performing the first process.

However, the automating equipment for the first process is too expensive, and has been hardly spread at present.

Practically in many cases, the pretreatment tends to be performed by means of a manual method capable of carried out more cheaply than the automating equipment.

However, since the manual method requires a mastery of arts, such as how to handle equipment (e.g. a centrifugal machine and/or a micropipette), the sample, or the like, the operational burden on the operator must be heavy.

Neither a method nor a kit is known which can simplify the manual method so as to be used in the POCT mode.

As for one representative solid-phase extraction method used in the automating equipment, there is a method reported by Boom et al (hereinafter, called as the "BOOM method". See, Reference 1 and Reference 5.).

The BOOM method is the solid-phase extraction method for isolating nucleic-acid from a biological sample according to a principle based on chaotropic effects (See, Reference 6.) caused by a phenomenon that the nucleic-acid absorbs silica beads in the presence of a chaotropic agent.

According to the BOOM method, without making nucleic-acid elute from a solid-phase carrier, the nucleic-acid can be added to PCR solution together with the solid-phase carrier (See, Reference 2.), and a part of elution process can also be simplified. The BOOM method, however, assumes that environment for performing the extraction of nucleic-acid, such as an inspecting room, has been prepared.

Reference 3 recites as follows. Namely, "An object according to the present invention is to provide: a method of, without using organic solvent, simply, in a short time, further safely, and with high reproducibility extracting ribonucleic acid from biological material; and a reagent for the method. Dissimilar to deoxyribonucleic acid, upon washing with low salt concentration buffer solution containing no organic solvent (e.g. ethanol, or the like.) after having made ribonucleic acid absorb a solid-phase carrier, the ribonucleic acid hardly elutes from the solid-phase carrier. Once well-heated, however, the ribonucleic acid is promoted to elute there-from. A second process in the present invention is a process of washing a solid-phase carrier on which ribonucleic acid have absorbed due to a first absorption process by means of wash fluid composed of low salt concentration buffer solution in order to remove chaotropic material, or the like there-from. Herein, the <wash fluid composed of the low salt concentration buffer solution> means buffer solution containing neither organic solvent (e.g. ethanol, or the like.) nor chaotropic material. It is preferable that the buffer solution is Tris system buffer solution. However, the present invention is never limited to the Tris system buffer solution. The <low salt concentration> means a level of salt concentration that does not affect enzyme reaction (e.g. RT-PCR, or the like.) even when this buffer solution remains in the third elution process, and also includes water itself solely. Preferably in the present invention, 100 or less [mM] of buffer solution may be used. This solution may contain a surface active agent and pH thereof is not limited in particular. In the present invention, it is necessary to promote the elution by heating. Heating temperature is not limited in particular, as long as it does not cause adverse effects on the ribonucleic acid, but may be preferably 50 through 70 [Centigrade]. Hearing time is about 30 [s] through 10 [min]. The ribonucleic acid eluted in this way can be directly used for the enzyme reaction by means of reverse transcriptase or the like without performing: dialysis; desalting (e.g. according to an ethanol precipitation method, or the like.); or concentration operation (partially omitted)".

Reference 4 recites, "However, the present inventors have found that, in the elution process (3), making nucleic-acid elute with water and/or low salt concentration solution at 80 or more [Centigrade] enables to extract DNA, thereby having completed the present invention."

The methods recited in these References have the following disadvantages, and are difficult to be turned into the POCT mode.

Firstly, they require complicated operation with high difficulty, because a few through some hundreds [µl] of solution must be collected and added, contamination must be prevented according to accurate operation of pipets, and hazardous reagent must be dealt with.

Secondly, they also require: washing the target several times with wash fluid containing salt and/or organic solvent; and surely removing the organic solvent according to drying process therefrom.

They further require: performing the drying process while taking care of fixation between the nucleic-acid and the adsorbing carrier caused by excessive drying. Consequently, long time and great effort must be paid.

Thirdly, initial costs for preparing operation environment must be high, because they require: operation using the centrifugal machine and the micropipette; and an installation site and/or a working space for used equipment.

Reference 1: Japanese registered patent No. 2680462
Reference 2: Japanese patent application Laid-open No. 10-72485
Reference 3: Japanese registered patent No. 3812696
Reference 4: Japanese patent application Laid-open No. 2014-30364
Reference 5: R Boom et al, J. Clin Microbiol, 28 (3), 495-503 (1990)
Reference 6: B Vogelstein and D Gillespie, PNAS, 76 (2), 615-619 (1979)

OBJECTS AND SUMMARY OF THE INVENTION

In view of the above background, an object according to the present invention is to provide a method capable of realizing pretreatment process of genetic screening according to a POCT mode.

A first aspect of the present invention provides: a pretreatment method, comprising: making a sample, extraction liquid for extracting nucleic-acid contained in the sample, silica particles, and a filtering material contact with each other; making the filtering material carry composite material of the nucleic-acid and the silica particles thereon; and then delivering the filtering material to a nucleic-acid-amplifying process by means of reaction solution for amplifying nucleic-acid, wherein particle diameters of the silica particles and concentration of the silica particles in the reaction solution for amplifying nucleic-acid are set up within a predetermined range, thereby allowing, in advance of the nucleic-acid-amplifying process, to omit both a drying process and an elution process.

A second aspect of the present invention provides: in addition to the first aspect, the pretreatment method wherein the predetermined range is defined as follows: the concentration of the silica particles is 0.0625 through 4 [µg/µl]; an average particle diameter of the silica particles is 0.01 through 100 [µm]; and a surface area calculated based on the average particle diameter is $1 \times 10^4$ through $1 \times 10^8$ [µm].

A third aspect of the present invention provides: in addition to the first aspect, the pretreatment method wherein the predetermined range is defined as follows: the concentration of the silica particles is 0.0625 through 1 [µg/µl]; an average particle diameter of the silica particles is 0.01 through 10 [µm]; and a surface area calculated based on the average particle diameter is $1\times10^5$ through $5\times10^7$ [µm$^2$].

A fourth aspect of the present invention provides: in addition to the first aspect, the pretreatment method further comprising: a first extraction process of adding the sample to the extraction liquid to extract the nucleic-acid contained in the sample; a first absorption process of: making the silica particles contact with the extracted nucleic-acid to obtain the composite material of the nucleic-acid and the silica particles; and making the composite material contact with the filtering material; and a first washing process of: washing the composite material and the filtering material with purified water; and delivering the washed composite material and the washed filtering material to the nucleic-acid-amplifying process.

A fifth aspect of the present invention provides: in addition to the first aspect, the pretreatment method wherein, prior to the delivering the filtering material to the nucleic-acid-amplifying process, the composite material is separated from the filtering material, and then the separated composite material is delivered to the nucleic-acid-amplifying process.

A sixth aspect of the present invention provides: in addition to the fourth aspect, the pretreatment method wherein the first absorption process and the first washing process are performed at the same time.

A seventh aspect of the present invention provides: in addition to the fourth aspect, the pretreatment method wherein the first extraction process and the first absorption process are performed at the same time.

An eighth aspect of the present invention provides: in addition to the fourth aspect, the pretreatment method wherein the first extraction process, the first absorption process, and the first washing process are performed at the same time.

A ninth aspect of the present invention provides: in addition to the first aspect, the pretreatment method further comprising: a second extraction process of adding the sample to the extraction liquid to extract the nucleic-acid contained in the sample; a second absorption process of: making the extracted nucleic-acid contact with the filtering material carrying the silica particles thereon to obtain the composite material of the nucleic-acid and the silica particles; and making the filtering material carry the obtained composite material thereon; and a second washing process of: washing the carried composite material and the filtering material with purified water; and delivering the washed composite material and the washed filtering material to the nucleic-acid-amplifying process.

A tenth aspect of the present invention provides: in addition to the ninth aspect, the pretreatment method wherein, prior to the delivering the filtering material to the nucleic-acid-amplifying process, the composite material are separated from the filtering material, and then the separated composite material is delivered to the nucleic-acid-amplifying process.

An eleventh aspect of the present invention provides: in addition to the ninth aspect, the pretreatment method wherein the second absorption process and the second washing process are performed at the same time.

Effect of the Invention

With the methods according to the present invention, the following effects can be obtained.

Firstly, the extraction process of nucleic-acid in genetic screening can be simple, easy, safe, rapid, and less expensive, and capable of realizing the process of according to the POCT mode.

Secondly, the combination of safe, simple, and easy operation enables to remarkably shorten operation time comparing with the conventional methods, and further the extraction of nucleic-acid can be performed at a low cost.

This is because the purified water is used as the wash fluid. Accordingly, it is unnecessary to prepare a plurality of kinds of organic solvent. It is also unnecessary to use the plurality of kinds of organic solvent while distinguishing thereof from each other. Furthermore, the organic solvent itself is unnecessary, and the operation is easy and safe.

Thirdly, since the organic solvent itself is unnecessary, both drying operation upon the solid-phase carrier and the elution process of nucleic-acid can be omitted.

In short, immediately after the washing process, the target can be delivered to the nucleic-acid amplification reaction.

In addition, since the time of transfer of the solution can be remarkably reduced, environmental risks, such as splashes of nucleic-acid and/or cross contamination can be also reduced.

BRIEF DESCRIPTION OF SYMBOLS

Figure 1:
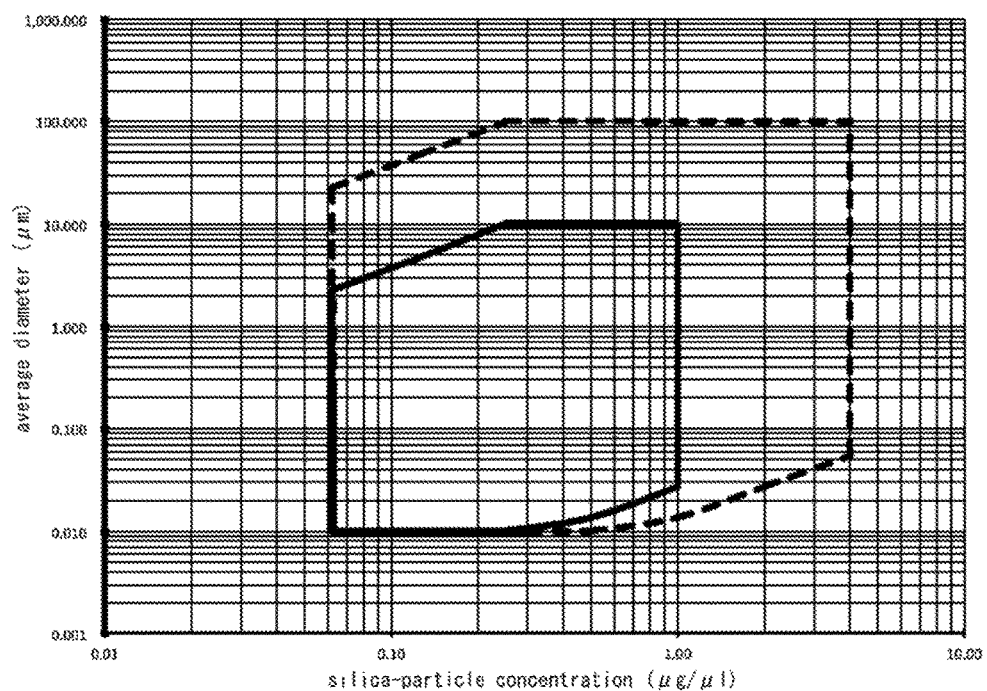
FIG. 1 is a graph showing a predetermined range according to the present invention.

2: Funnel portion
3: Filtering material
4: First water absorption material
5: Second water absorption material
6: Adjusting member
7: Housing
10: Tube
11: Extraction liquid
12: Sample
13: Nucleic-acid
14: Silica particle
15: Composite material
16: Purified water

DETAILED DESCRIPTION OF THE PREFERRED EMBODIMENTS

Main Points of the Invention

Firstly, prior to the concrete description of Embodiments, main points of the present invention will now be described.

In order to solve the above-mentioned problems, the present inventors have broken away from a "method of collecting nucleic-acid as much as possible from a sample to be used for extracting nucleic-acid", which is often seen in the conventional methods, and have eagerly studied how to solve the problems while focusing on how to secure a minimum necessary amount of nucleic acid in one test for nucleic-acid amplification reaction.

As a result of the above consideration, the present inventors have found the following pretreatment method of nucleic-acid to complete the present invention, thereby solving the above mentioned problems.

That is, the pretreatment method includes:

a first step (a) (hereinafter, called "extraction process.") of extracting nucleic-acid from a sample with means that the person skilled in the art can conceive including: a chaotropic agent; salt; acid; alkali; a surface active agent; organic solvent; enzyme; french press; heating; and a ultrasonic wave:

a second step (b) (hereinafter, called "absorption process.") of, after the step (a), making a solid-phase carrier absorb the extracted nucleic-acid;

a third step (c) (hereinafter, called "washing process.") of washing and removing contaminant absorbed on the solid-phase carrier with purified water; and a fourth step (d) of, immediately after the washing process, adding the nucleic-acid together with the solid-phase carrier into reaction solution. In this way, the nucleic-acid amplification reaction can be performed without any problems.

Furthermore, the present inventors, by applying the invented pretreatment method, have found that using a combination of: a filter device including the filtering material and water absorption material therein; and a solid-phase carrier, enables to perform extract nucleic-acid even at a place where tests in the POCT are carried out.

In conclusion, the present inventors have achieved a nucleic-acid-extracting kit applicable for the method including: the washing process with purified water; and the above process of adding the nucleic-acid together with the filtering material into the reaction solution.

Embodiments of the Present Invention

Hereinafter, before showing detailed consideration, the conclusion of the present invention will now be described.

The pretreatment method according to the present invention enables to carry out the nucleic-acid amplification reaction immediately after the washing process.

As a method of separating liquid, such as wash fluid, from the solid-phase carrier on which nucleic-acid have been absorbed, a separation method by means of centrifuge separation and/or a centrifugal column, a filtering separation method, or the like may be used.

Upon using silica particles containing magnetic material, of course, a separation method using magnetic force may be also possible.

In the present invention, the solid-phase carrier may be composed of silica particles.

According to the present invention, the nucleic-acid and silica particles (hereinafter, called "composite material of nucleic-acid+silica particles".) that have absorbed with each other in the absorption process may be contacted with nucleic-acid amplification reaction reagent solution immediately after the washing process to start the nucleic-acid amplification reaction.

FIG. 1 is a graph showing a predetermined range according to the present invention.

To say conclusions first, it is preferable that there are the silica particles existing in the reaction solution for amplifying nucleic-acid within a range enclosed with dotted lines in FIG. 1.

In FIG. 1, a horizontal axis thereof shows silica-particle concentration in the reaction solution for amplifying nucleic-acid, and a vertical axis thereof indicates an average particle diameter of the silica particles, respectively.

More concretely, a preferable predetermined range (a range enclosed with dotted lines in FIG. 1) is as follows: the concentration of the silica particles is 0.0625 through 4 [µg/µl]; the average particle diameter of the silica particles is 0.01 through 100 [µm]; and a surface area calculated based on the average particle diameter is $1 \times 10^4$ through $1 \times 10^8$ [µm$^2$].

A further preferable predetermined range (another range enclosed with solid lines in FIG. 1) is as follows: the concentration of the silica particles is 0.0625 through 1 [µg/µl]; the average particle diameter of the silica particles is 0.01 through 10 [µm]; and the surface area calculated based on the average particle diameter is $1 \times 10^5$ through $5 \times 10^7$ [µm$^2$].

It is sufficient that the sample in the present invention is material which may contain nucleic-acid, for example, which may be a specimen sample extracted upon diagnosis of infectious disease.

The specimen sample with respect to the infectious disease may be one of specimens extracted when infectious disease is suspected, including: pharynx-wiping liquid; nasal cavity-wiping liquid; urological material (various kinds of urine specimens); reproductive material; feces; blood; or the like.

The nucleic-acid may include: nucleic-acid derived from pathogenic microorganisms that the person skilled in the art can conceive as a template for nucleic-acid amplification reaction, such as DNA (dsDNA, ssDNA) and RNA (dsRNA, ssRNA); and endogenous nucleic-acid derived from microorganisms producing the specimen sample.

Furthermore, the samples with respect to the nucleic-acid may also include not only the specimen samples extracted upon the diagnosis of infectious disease but also samples that may contain nucleic-acid collected at other various locations.

For example, it is conceivable to use the samples for food evaluation (detecting food poisoning offending bacteria, recombinant genes, or the like.), infectious disease inspection of farm products, water quality inspection of drinking water, water quality inspection at factories, or the like.

However, the above are mere examples, and the present invention is not limited thereby.

It is assumed that a nucleic-acid sample of the present invention treats 1 or less [µg] of nucleic-acid amount, and 1 [ag] through 100 [ng], preferably an about 1 [pg] through 10 [ng] quantity of nucleic-acid is assumed to be delivered to the reaction solution for amplifying nucleic-acid.

In the present invention, the extraction process is performed by:

obtaining nucleic-acid-containing solution according to a nucleic-acid-extracting method using a chaotropic agent, salt, acid, alkali, a surface active agent, organic solvent, enzyme, french press, heating, a ultrasonic wave, or the like; and adding silica particles into the obtained nucleic-acid-containing solution, directly, after having diluted the same, or after having replacing the same.

In the pretreatment, the absorption process and the extraction process may also be carried out at the same time.

In the present invention, the wash fluid used for the washing process may be purified water.

The purified water may be water purified by one of various methods, and includes water applicable for reagent preparation that the person skilled in the art can normally conceive upon performing the nucleic-acid amplification reaction.

The purified water is water containing neither organic solvent nor nucleic-acid amplification reaction inhibition material, such as high-concentration salt.

In the present invention, the washing process is carried out by washing the target with a proper quantity of the purified water after the absorption process.

How many times the washing process should be performed is not limited, and may be normally once through several times.

Immediately after the washing process, the composite material of nucleic-acid+silica particles is added to the nucleic-acid amplification reaction reagent solution.

However, the washing process can be omitted in a case where the purified water is used as solvent in the absorption process, or in another case where the nucleic-acid-containing solution obtained after the absorption process is diluted or replaced with the purified water.

In the present invention, the filtering material for filtering separation may have a pore size that absorbs nucleic-acid less and further that can filter the above silica particles among those normally selected by the person skilled in the art, such as a membrane filter, or the like.

For example, a film, a membrane filter, a textile, a non-woven fabric, or the like each of which is made of poly-lactic acid, cellulose, PTFE, or the like can be adduced.

A shape of the filtering material is not limited to a film, may be any one applicable for filtering, for example, a bag, a tube, or the like.

For example, the "Omnipore (trademark)" membrane filter (JCWP) produced by the Merck "Japan Millipore" corporation, or the like is preferable.

In the present invention, since the filtering separation utilizes the filtration device that includes the water absorption material therein, extraction of nucleic-acid in the POCT mode can be realized.

Regarding the filtration device that includes the water absorption material therein, solution, such as wash fluid, flows in a one-way direction, and the water absorption material provided with the inside thereof absorbs the used solution so as to prevent from splashes of the liquid to the outside thereof.

The present invention is carried out pursuant to standard technique for the person skilled in the art with respect to points without special explanation in Embodiments and Examples.

For example, the present invention is configured referring to methods recited in "Molecular Cloning A LABORATORY MANUAL FOURTH EDITION (Green and Sambrook, the Cold Spring Harbor Laboratory Press)", "Cell technologies separated volume bio-experiment illustrated series" (the Gakken Medical Shujunsha Co., Ltd.), or "the revised third edition genetic engineering experiment note" (Takaaki TAMURA/editor, upper and lower volume, the YODOSHA CO., LTD.), or the like.

Furthermore, commercial reagent and devices are used according to the attached protocol thereof with respect to points, if not especially explained.

Examples shown below are mere illustration of one Embodiment of the present invention for explaining the present invention in detail, and the present invention is not limited thereby.

Example 1

<Material and Method>
(Purified Water)

Ultra-pure water obtained using the "Direct-Q (registered trademark)" 5UV ultra-pure water system (the Merck KGaA) has been used for the purified water in Example 1.

TABLE 1

| silica particles No. (Name, PD No., Cat No.) | maker/vendor |
|---|---|
| 1  30925-12 | Nacalai Tesque, INC. |
| 2  Microsilica (®) Grade 971 | Elkem Japan Kabusiki Kaisya |
| 3  SIO07PB | Kojundo Chemical Lab. Co., Ltd. |
| 4  s5631 | Sigma-Aldrich Co. LLC. |
| 5  HS-301 | Nippon Steel & Sumikin Materials (Micron) |
| 6  SIO14PB | Kojundo Chemical Lab. Co., Ltd. |
| 7  SIO08PB | Kojundo Chemical Lab. Co., Ltd. |
| 8  NanoSilica Powder Grade 999 | Elkem Japan Kabusiki Kaisya |
| 9  SR-NP (200P) | Mtec-chem Kabusiki Kaisya |
| 10 SR-NP1 (200P1) | Mtec-chem Kabusiki Kaisya |
| 11 TECNAPOW-SIO2-100G | ARBROWN Co., LTD. (TECNAN) |
| 12 silicon dioxide, 99.9% | Wako Pure Chemincal Industries, Ltd. |

(Solid-Phase Carrier)

The solid-phase carrier in this Example has been composed of silica particles.

Table 1 shows product identification information (such as the name of the used silica particles, the product number, the catalog number, or the like.), and (maker and vendor) company information.

Items are shown while giving numbers in order from the greatest value of average particle diameters according to information attached to the catalog and/or the product thereof, such as an analysis certificate.

However, Table 1 merely shows silica particles used in Example 1, and does not limit silica particles in the present invention.

(Nucleic-Acid Sample)

Regarding the nucleic-acid sample in this Example, a detection target has been determined to be a "p1" gene derived from *Mycoplasma pneumoniae* becoming a cause of *mycoplasma pneumonia*.

The nucleic-acid sample has been produced by: incorporating a fragment of the "p1" gene derived from *Mycoplasma pneumoniae* into pUC57 plasmid DNA using a conventional method to obtain the incorporated DNA, thereby cloning it.

The produced nucleic-acid sample has been prepared into 3 [pg/μl] concentration with TE buffer solution.

After the preparation, the nucleic-acid sample has been used as a standard sample for generating a calibration curve upon performing real-time quantitative PCR, or the like.

After having dispensed a part of the prepared nucleic-acid sample, the part has been further diluted with the TE buffer solution to be prepared into 3[pg]/50[μl] of concentration, and has been used as starting material upon extracting nucleic-acid.

(Primer and Probe)

As primers, "primer sets for a "P1" adhisin gene each including:

5'-GCCACCCTCGGGGGCAGTCAG-3'; (SEQ ID NO: 1)
and
5'-GAGTCGGGATTCCCCGCGGAGG-3'" (SEQ ID NO: 2)

have been used, which have been recited in the report ("The Journal of Infectious Diseases", 1996; 173; 1445-52) by Ieven et al.

After having selected a specific region from amplified products by means of the above-mentioned primer sets, the probes have been produced according to a method normally used by the person skilled in the art.

Production of the probe has been performed by requesting custom synthesis of QProbe (registered trademark) to the J-BIO21 center of the NIPPON STEEL & SUMIKIN Eco-Tech Corporation.

(Preparation of Other Reagents)

As the other reagents, commercial reagents have been used to be prepared according to a method normally used by the person skilled in the art.

"Lysis buffer L6" has been used for lysis liquid upon reproducing at least a part of the BOOM method.

The "lysis solution L6" has been prepared according to the method recited in Reference 1.

(Nucleic-Acid Amplification Reaction and Analyzing Method for the Same)

As the nucleic-acid amplification reaction, the real-time quantitative PCR has been performed with 20 [μl/tube] amounts of reaction solution.

"LightCycler (registered trademark)" nano system (the Roche Diagnostics K.K.) has been used for an instrument.

The reaction profile has been performed including: at 95 [Centigrade] and 120 [s] of an initial denaturalization program; at 95 [Centigrade] and 10 [s] of a first amplification program; at 68 [Centigrade] and 10 [s] of a second amplification program; and at 72 [Centigrade] and 10 [s] of a third amplification program. The set of the first, the second, and the third amplification programs has been repeated by 40 [cycles].

The melting curve analysis program has been set up within a range 68 through 95 [Centigrade].

The real-time quantitative PCR has been carried out using the intercalator method and the probe method.

The intercalator method has been performed using pigment of "20×EvaGreen Dye" (registered trademark, The Biotium inc.), and the probe method has been carried out using "QProbe" (registered trademark of the NIPPON STEEL & SUMIKIN Eco-Tech Corporation).

After completion of the reaction, whether or not the obtained amplification curve corresponds to the target products derived from the subjected DNA has been confirmed based on the results of melting curve analysis program.

In the Example, the nucleic-acid amplification reaction has been carried out using the intercalator method, if not especially stated.

The intercalator method has been performs as follows:
selecting "Automatic Quantification," which is analysis software exclusive to the device;
checking, based on the calibration curve, whether or not PCR efficiency and the value of $R^2$ are within a normal range according to a conventional method; and
then analyzing the amplification curve based on obtained Ct values and quantitative values.

On the other hand, an analysis method provided with the "LightCycler" nano system cannot analyze a probe method belonging to a type of extinguishing light, such as the "QProbe." Therefore, with respect to this type, the raw data have been directly processed pursuant to methods recited in Japanese registered patent No. 4724380 to obtain Ct values and quantitative values. After that, analysis has been performed as described above.

As data for the analysis, an average of a plurality of data each of which has been obtained under the same condition has been used.

Hereinafter, the details of Items 1 to 5 will now be concretely explained.

In each of the following Items, technical subjects, countermeasures, results, and consideration related thereto will be shown.

Item 1: Practical Influence when changing wash fluid to purified water

Item 2: Influence on nucleic-acid amplification reaction caused by adding silica particles Item 3: Influence on nucleic-acid amplification reaction when amount of added silica particles changes Item 4: Influence on absorbing capability and nucleic-acid amplification reaction caused by amount of used amount of silica particles Item 5: Influence caused by chaotropic agent in absorption process and operation with simple filtration device (Item 1)

In Item 1, whether or not changing all of "L2", "70% ethanol," and "acetone" into purified water is possible has been examined. Herein, the "L2", the "70% ethanol," and the "acetone" are used as wash fluid in the washing process regarding protocol "Y" recited in Reference 1 (hereinafter, called "the protocol Y.") in the BOOM method. And, whether or not other conditions can be performed pursuant to the protocol Y has been also examined.

As "starting material" in the protocol Y, 3 [pg]/50[μl] concentration of prepared nucleic-acid sample has been used.

Silica-particles of No. 4 in Table 1 have been used as the silica particles, and have been prepared according to "suspension preparation of silica rough material (SC)" recited in "material and methods" of Reference 1.

After extraction, 2 [μl] of the obtained effluent has been dispensed to be added to 18 [μl] of PCR reagent solution, thereby preparing so as to be 20 [μl] total quantity of PCR solution.

Real-time quantitative PCR has been applied on the prepared PCR solution to obtain quantitative values.

The obtained quantitative values have been multiplied by 25 to obtain nucleic-acid amounts collected per one tube, repeatedly. And, an average thereof has been calculated.

Based on 100% of 3 [pg] quantity of nucleic-acid contained in the starting material, percentage in the above has been calculated to obtain recovery percentage (%).

TABLE 2

| | DNA recovery (%) | |
|---|---|---|
| | Ave per tube (%) | per 10 μl (&) effluent |
| Item 1 | 1.99 | 0.40 |
| Prior art | 78.59 | 15.72 |
| +reference | 100.00 | 20.00 |

Table 2 shows average recovery percentage per one tube (%) and recovery percentage (%) per 10 [μl] of effluent.

In the positive reference of Table 2, a value when 100% of 3 [pg] contained in the starting material has been collected is shown for reference.

As a conventional Example (Prior art), the BOOM method according to the protocol Y has been carried out.

Based on the obtained quantitative values, the recovery percentage (%) has been calculated in the same way as Item 1.

Table 2 shows average recovery percentage per one tube (%) and recovery percentage (%) per 10 [μl] of effluent, together with the results of Item 1.

As seen from Table 2, when the wash fluid is wholly changed into purified water, the recovery percentage of nucleic-acid remarkably falls (78.59%: the conventional Example, 1.99%: Item 1).

It is newly understood that simply changing wash fluid into purified water has the same meaning as general elution operation, thereby washing out even nucleic-acid absorbed onto the silica particles.

Although data has been not shown, the recovery percentage tends to fall in a case when the starting material is less (e.g. 3 [pg]) comparing with another case where the starting material is more (e.g. handled in a unit [μg]).

It can be guessed that at the maximum 10 [μl] of effluent can be added to the PCR solution in Item 1. Even in this case, it is considered that 0.40% of 3 [pg], that is, only about 12 [fg] can be delivered into the reaction solution for amplifying nucleic-acid.

On the other hand, considering in the same way, in the conventional Example, 15.72% of 3 [pg], that is, about 470 [fg] can be delivered there-into.

As seen from the above, when the wash fluid in the protocol Y of the BOOM method is simply changed into water only, a sufficient amount of nucleic-acid cannot be obtained.

As revealed by the results of the conventional Example in Table 2, if about 5 through 15% can be recovered from the start material containing 3 [pg] amount of nucleic-acid, an enough amount capable of being detected in nucleic-acid amplification reaction for one test can be obtained.

In the present invention, in a case where low concentration of nucleic-acid effluent has been obtained, it is difficult to select concentration operation and/or solution replacement by means of an ethanol precipitation method, concentration columns, or the like. This is because such selection makes the operation more complicated and burdensome.

Referring to the above-mentioned results, it can be considered that the method of simply changing the wash fluid in the washing process of the BOOM method to purified water is insufficient in a case where a nucleic-acid amount of the starting material is less, and/or in another case where low concentration of nucleic-acid effluent has been obtained.

Whereas, if washing the target by means of purified water is available, various kinds of advantages may be acquired.

According to the BOOM method, or the like above-described as the conventional Example, complicated and time-consuming operation is necessary. The necessary operation may include: removing contaminant so as to obtain pure nucleic-acid solution; washing the target several times using a plurality of kinds of wash fluid, and then drying the washed target, thereby removing salt used for the adsorption; or the like.

If washing the target with the purified water is available, almost all of the necessary operation can be omitted.

In addition, the composite material of nucleic-acid+silica particles can be delivered to the next nucleic-acid amplification reaction under a wet condition. Accordingly, it is unnecessary to worry that the nucleic-acid is too strongly fixed onto the silica particles because of a dried condition.

Furthermore, since the nucleic-acid can be extracted by the simple operation, easy operation can be presented to also operators who are not familiar with operation, such as the genetic screening. And, it is unnecessary to worry that the nucleic-acid is strongly fixed onto the silica particles under the dried condition, small silica particles with high nucleic-acid-absorbing capability can also be effectively used.

Using the silica particles each having a small particle diameter enables to remarkably reduce an amount of silica particles to be used for the solid-phase carrier.

(Item 2)

In Item 2, it has been examined how adding silica particles affects to the nucleic-acid amplification reaction. This has been performed in a reaction system using 20 [μl] total quantity of real-time quantitative PCR solution, with 5 [μg/tube] of silica particles and 3 [pg/tube] of nucleic-acid sample to obtain the Ct value.

For the comparison of the Ct values, a positive reference ((0 [μg/tube] of silica particles), a positive nucleic-acid sample (3 [pg/tube])), a negative reference ((0 [μg/tube] of silica particles), and 0 [pg/tube] of a negative nucleic-acid sample) have been prepared.

With respect to the positive reference, in order to obtain the standard of Ct values, a first average value has been calculated based on the obtained Ct values, and the first average value has been defined as 100%.

Similar to the above, a second average value has been calculated based on Ct values obtained related to the respective silica particle. And then, the changing ratio (%) of Ct values has been calculated by:

dividing the second average value by the first average value to obtain a quotient; and multiplying the quotient by 100.

In Item 2, dissimilar to Item 1, all of the silica particles on sale have been used as they are, that is, without performing reform operation on the particles, such as regulating ranges of particle diameters used silica particles or modifying surfaces thereof.

The determined amount of silica particles for use has been prepared with suspension preparation of silica particles into proper concentration capable of being easily dispensed.

(Item 3)

In Item 3, pursuant to Item 2, influence on the nucleic-acid amplification reaction caused by added amounts of the respective silica particle has been examined.

10 [μg], 20 [μg], and 40 [μg] amounts per PCR tube of the silica particles have been added to prepare 20 [μl] total amount of real-time quantitative PCR solution, and then the examination has been carried out.

TABLE 3

| | changing ratio of Ct values (%) | | | |
|---|---|---|---|---|
| No | 5 μg/tube 0.25 μg/μl$^{\times 1}$ | 10 μg/tube 0.50 μg/μl$^{\times 1}$ | 20 μg/tube 1.00 μg/μl$^{\times 1}$ | 40 μg/tube 2.00 μg/μl$^{\times 1}$ |
| 1 | 101.3 | 100.8 | 100.8 | 100.7 |
| 2 | 101.2 | 101.0 | 100.8 | 100.9 |
| 3 | 101.2 | 100.9 | 99.5 | 102.0 |
| 4 | 102.6 | 113.3 | n/a | n/a |
| 5 | 102.2 | 102.2 | 102.7 | 105.6 |
| 6 | 102.1 | 102.5 | 102.3 | 103.5 |
| 7 | 101.9 | 107.7 | 116.4 | 155.3 |
| 8 | 105.2 | 111.3 | 133.6 | n/a |
| 9 | 106.3 | 119.2 | 154.1 | n/a |
| 10 | 101.3 | 102.1 | 104.2 | 113.5 |

TABLE 3-continued

| | changing ratio of Ct values (%) | | | |
|---|---|---|---|---|
| No | 5 µg/tube 0.25 µg/µl[*1] | 10 µg/tube 0.50 µg/µl[*1] | 20 µg/tube 1.00 µg/µl[*1] | 40 µg/tube 2.00 µg/µl[*1] |
| 11 | 110.4 | 147.5 | n/a | n/a |
| 12 | 104.3 | 115.6 | 132.4 | n/a |
| +ref | 100.0 | 100.0 | 100.0 | 100.0 |
| −ref | 150.9 | 134.0 | 132.4 | 130.0 |

Table 3 shows the results of Item 2 and Item 3 together.

With respect to Item 2, comparing cells of Table 3 in a vertical direction enables to recognize differences caused by the respective used silica particle under the same used amount condition.

With respect to Item 3, comparing cells of Table 3 in a horizontal direction enables to recognize influence on the real-time quantitative PCR when an amount of the silica particles existing in the real-time quantitative PCR solution changes.

In Table 3, a symbol of "n/a" means that no data exists, and another symbol of "*1" means an amount ([µg]) of silica particles per 1 [µl] of real-time quantitative PCR solution, respectively.

The results of Item 2 (5 [µg/tube]) reveal that, even when 0.25 [µg] amount of silica particles are contained in a unit of 1 [µl] of the real-time quantitative PCR solution, there is a case with serious influence (the change ratio of Ct values exceeds 10%) on the real-time quantitative PCR.

There are some used conditions which can be estimated almost within dispersion of the Ct values (e.g. 2% or less of changing ratio of Ct values) among all of the used conditions.

The present inventors, referring to the results, have started studies of Item 3.

In Item 3, in response to the results of Item 2, comparison while changing used amounts of the silica particles has been carried out.

The results of Item 3 reveal the followings. That is, the smaller the average particle diameters with higher nucleic-acid absorbing capability are, the larger the changing ratio of Ct values tends to become, as the used amounts increase. In other words, the greater the average particle diameters are, the less change tends to be observed.

In the case of the "suspension preparation of silica rough material (SC)" for reproducing the protocol Y in the BOOM method, the amount of used silica particles in the conventional Example of Item 1 corresponds to about 30 through 50% of silica-particle suspension preparation.

Accordingly, it is estimated that the amount of silica particles existing, upon performing extraction, in one tube is about 12 through 20 [mg].

Even if taking the difference regarding the used silica particles into consideration so as to estimate necessary volume of silica particles to be used as less as possible, it is considered that about one or more [mg] of silica particles are required for reproducing the BOOM method.

In Reference 2, after having applied a solid-phase carrier absorbed by nucleic-acid into suspension preparation, ⅖ amount thereof is directly added there-into, and then the PCR is carried out.

At that time, as for the silica particles existing in the PCR solution, about at least 200 [µg] of silica particles exist in the 50 [µl] of PCR solution (that is, 4.00 [µg/µl]) according to the BOOM method.

Whereas, in Item 2 and Item 3, at most 40 [µg] of the silica particles exist in the 20 [µl] of real-time quantitative PCR solution (that is, 2.00 [µg/µl]).

Referring to the results of Item 2 and Item 3, the followings are considered according to the BOOM method. Since the amount of used silica particles is too much, the nucleic-acid amplification reaction is considered to have a possibility of being strongly inhibited upon having delivered all of used solid-phase carriers to the next operation.

The BOOM method assumes the large amount of solid-phase carriers, and may be wasteful in handling the start material containing one or less [µg] of nucleic-acid. This is because the method requires either eluting the nucleic-acid or dispensing, without eluting the same, a part of the solid-phase carriers to prepare the amount of used silica particles.

The dispensing operation is essential and complicated. The method forces the difficult operation even on operators who are not familiar with handling nucleic-acid (e.g. extracting the nucleic-acid).

It is considered that the BOOM method is not available to cases, including: a first case where about 1 [ag] through 500 [ng] amount of nucleic-acid is contained in a specimen (e.g. rapid diagnosis of infectious disease); a second case where simple and quick operation is required; and a third case where simple and plain operation is needed.

Referring to the results of Item 2 and Item 3, it is considered as follows. That is, extracting nucleic-acid can be rapidly performed only by the simple and plain operation if a condition:

wherein an amount of silica particles is adjusted to secure a necessary amount of the nucleic-acid; and further wherein a used range is limited such that the nucleic-acid amplification reaction is never or hardly inhibited, is fulfilled.

(Item 4)

In Item 4, the illustrated silica particles will now be examined whether or not they can be practically used for the pretreatment.

Processes until the washing process have been carried out according to Item 1.

Silica suspension has been adjusted so that, in 40 [µl] of the purified water, 1.25 [µg], 2.5 [µg], 5 [µg], 10 [µg], 20 [µg], 40[µg], and 80 [µg] of silica particles have been contained, respectively.

Immediately after the washing process, the composite material of nucleic-acid+silica particles has been suspended with 5 [µl] of purified water to obtain suspension preparation containing the composite material of nucleic-acid+silica particles.

All of the nucleic-acid+silica composite-material suspension preparation has been added to 15 [µl] of real-time quantitative PCR reagent to perform the real-time quantitative PCR.

After having completed the reaction, as quantitative values of silica particles under the respective used amount condition, averages related thereto have been calculated.

As another quantitative value regarding the obtained averages, recovery percentages have been calculated while having defined an average of quantitative values directly calculated based on the starting material as 100%.

TABLE 4

| | | recovery percentage after pretreatment | | | | | | |
|---|---|---|---|---|---|---|---|---|
| No. | Ave Diam (μm)*2 | 1.25 μg/tube 0.0625 μg/μl*1 | 2.5 μg/tube 0.125 μg/μl*1 | 5 μg/tube 0.25 μg/μl*1 | 10 μg/tube 0.50 μg/μl*1 | 20 μg/tube 1.00 μg/μl*1 | 40 μg/tube 2.00 μg/μl*1 | 80 μg/tube 4.00 μg/μl*1 |
| 1 | 74.000 | n/a | n/a | − | − | − | − | − |
| 3 | 5.266 | n/a | n/a | + | − | ++ | + | − |
| 4 | 3.450 | + | n/a | ++ | + | − | − | n/a |
| 5 | 2.550 | n/a | + | +++ | ++ | +++ | + | − |
| 6 | 1.900 | n/a | + | ++ | ++ | +++ | ++ | + |
| 7 | 0.670 | − | n/a | ++ | + | + | − | n/a |
| 8 | 0.400 | − | − | + | + | − | − | n/a |
| 9 | 0.286 | ++ | +++ | ++ | + | − | − | n/a |
| 10 | 0.229 | ++ | n/a | ++ | − | − | − | n/a |
| 11 | 0.014 | +++ | + | ++ | − | − | − | n/a |
| 12 | 0.012 | ++ | n/a | + | − | − | − | n/a |

+++: 20% or more
++: 10%~20%
+: 5%~10%
−: 5% or less

The recovery percentages have been evaluated according to a criterion that objects, having 5% or more of recovery percentage, have been regarded as objects to be evaluated, and have been recorded in Table 4 together with the criterion.

In Table 4, a symbol of "n/a" means that no data exists, and another symbol of "*1" means an amount [μg] of silica particles per 1 [μl] of real-time quantitative PCR solution, respectively.

And, a symbol of "*2" means an average particle diameter, which may be based on inspection reports attached with purchased products, or may be, without any attached inspection reports, based on an average particle diameter disclosed in catalogs, homepages, or the like.

The recovery percentages in Item 4 is for synthetically evaluating the property of silica particles in the pretreatment method of performing the washing process by means of the purified water, and show the influence of the silica particles from pretreatment through an amplification reaction process.

Regarding the pretreatment method, the percentages show, for example, absorption capability of silica particles in the absorption process, capability of retaining nucleic-acid in the washing process upon being exposed to the purified water, or the like, respectively.

The percentages in the nucleic-acid amplification reaction are what have been synthetically evaluated regarding: an inhibiting rate of real-time quantitative PCR; an inhibiting rate of fluorescence detection in the real-time quantitative PCR; or the like.

In Table 4, the more symbols of "+" are attached, the better recovery percentage is.

10% or more of results (attached symbols of "++" or "+++") have been recognized within the following ranges, including: a first range within near 0.3 [μm] or less of particle diameter under a first condition of 1.25 through 2.5 [μg/tube]; a second range within 0.01 through 3 [μm] of particle diameter under a second condition of 5 [μg/tube]; a third range within 1 through 5.3 [μm] of particle diameter under a third condition of 10 through 20 [μg/tube]; and a fourth range near 1.9 [μm] of particle diameter under a fourth condition of 40 [μg/tube].

Whereas, unfortunately, under a fifth condition of 80 [μg/tube], no good result has been recognized within the examined ranges.

According to Item 4, it has been shown that relationship between used amounts of silica particles (the solid-phase carrier) and particle diameters thereof may cause the results to greatly differ.

In other words, it has been suggested that properly preparing the amounts of the silica particles to be used enables to secure an enough amount of nucleic-acid regarding one test for the nucleic-acid amplification reaction without unfavorable influence, such as inhibiting the nucleic-acid amplification reaction, or the like. This is established even when the purified water has been used as the wash fluid and further when all of the used composite material of nucleic-acid+ silica particles have been added into the nucleic-acid amplification reaction reagent.

In Item 4, many of particle diameters showing good results belong to a range within 1 through 10 [μm], which have been pointed out as a preferable condition in many methods, such as the BOOM method.

Herein, conventional methods (See, References 1 through 4.), such as the BOOM method, recites that silica particles within a range of 0.05 through 500 [μm] can be used.

However, Reference 1 recites "Practically, the smaller the particles are, the higher NA-containing amounts arc. Especially, in a case where the start material has a high NA-containing amount, where NA molecules are comparatively long, and where too small silica particles are seed, the formed composite material of NA-silica cannot re-disperse any more. In other words, conjugated NA cannot be recovered in its form from the composite material (Note that the word of "NA" means nucleic-acid.)." Reference 1 seems to be of opinion that small particle diameters should be avoided.

In addition, the conventional methods further assume that removing particles with 1 or less [μm] diameter as much as possible should be also performed upon preparing the "suspension preparation of silica rough material (SC)."

Contrary to the assumption of the conventional methods, as is clear from Item 4, good results can be also obtained even when silica particles with the average particle diameter of 1 or less [μm] are used.

The present inventors have repeated, with respect to Items 2, 3, and 4, reproducing tests using the intercalator method and reproducing tests using the probe method so as to investigate relationship between particle diameters of silica particles and used amount thereof wherein:

changing ratios of Ct values are less;
influence to the real-time quantitative PCR is less;
high recovery percentages can be obtained; and
good results are shown.

As a result, as shown in FIG. 1, the present inventors have finally succeeded in specifying a range to be used (the predetermined range) of the silica particles wherein; the nucleic-acid-amplifying process is not affected; and sufficient amounts of nucleic-acid can be secured.

Although the followings are a repetition of the above, as shown with dotted lines of FIG. 1, the preferable predetermined range is defined as follows:

the concentration of the silica particles is 0.0625 through 4 [μg/μl];

the average particle diameter of the silica particles is 0.01 through 100 (μm): and a surface area calculated based on the average diameter is $1 \times 10^4$ through $1 \times 10^8$ [μm$^2$].

As shown with solid lines of FIG. 1, the further preferable predetermined range is defined is as follows:

the concentration of the silica particles is 0.0625 through 1 [μg/μl];

the average particle diameter of the silica particles is 0.01 through 10 [μm]; and the surface area calculated based on the average particle diameter is $1 \times 10^5$ through $5 \times 10^7$ [μm$^2$].

After having obtained the above results, the present inventors have assumed that not only adsorption phenomenon between nucleic-acid and silica particles according to the chaotropic effects but also phenomena other than the above, such as electrostatic force, intermolecular force, or the like caused by the structure of the silica particles are effective.

In order to confirm whether the assumption is true or false, the present inventors have investigated, without containing any of: salt (e.g. a chaotropic agent, or other salt increasing electrostatic force); and organic solvent, whether or not the extraction can be effectively performed.

According to the investigation, the present inventors have obtained a result that the extraction can be effectively performed without containing any of: the salt (e.g. the chaotropic agent, or the other salt increasing the electrostatic force); and the organic solvent.

Although the recovery percentages have slightly fallen comparing with a case where the chaotropic salt is used, a practically sufficient result has been obtained. Furthermore, it has been proven that using filtering separation together enables to make the extraction more effective.

(Item 5)

In Item 5, influence by the chaotropic agent in the absorption process has been investigated. And, using a simple filtration device shown in FIG. 2 (e), whether or not the device can be made to be used in the POCT mode has been studied.

Figure 2:
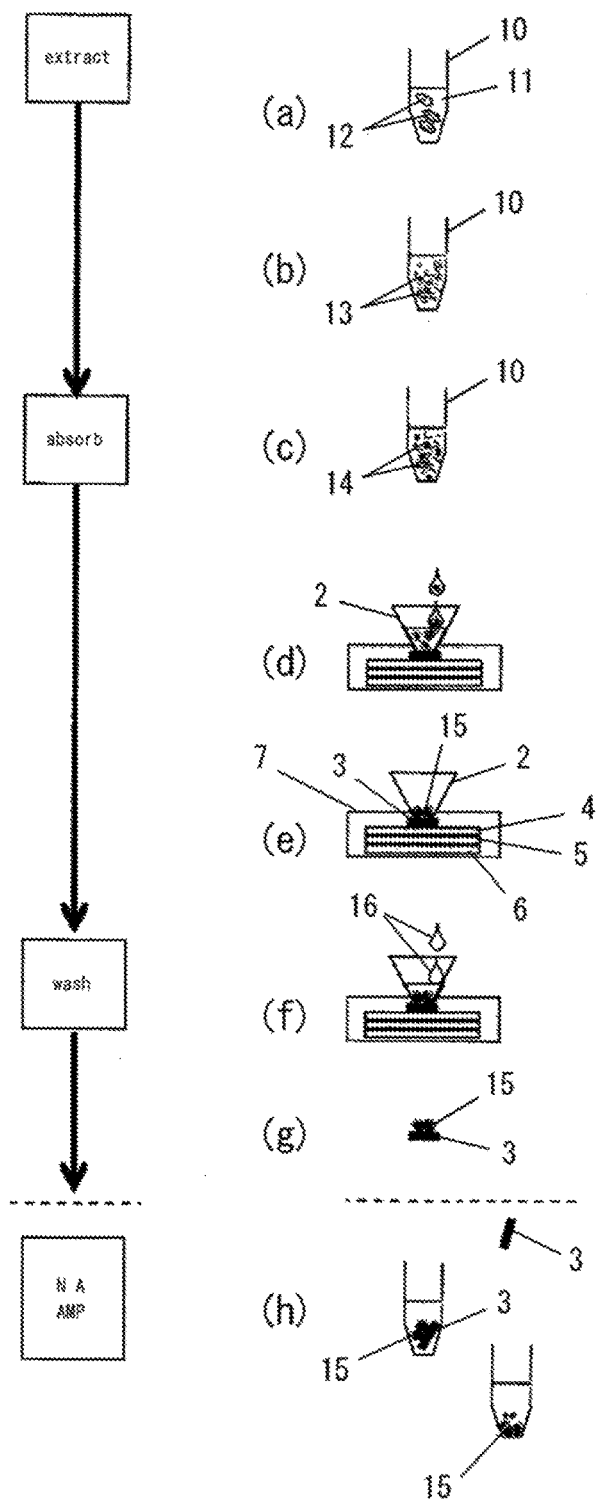
FIG. 2 shows processes of a pretreatment method in Embodiment 1 according to the present invention.

As shown in FIG. 2 (e), this filtration device includes: a housing 7 in a shape of a rectangle box, and a funnel part 2 fixed onto an upper center of the housing 7. And, in the inside of the housing 7, a laminated structure is provided including: a filtering material 3; first water absorption material 4; second water absorption material 5; and an adjusting member 6.

As the housing 7, a member capable of being easily processed, such as a commercial plastic box, may be used.

In this Example, "PP small soap case" (product number: 47697681, size: about 64 [mm]×52 [mm]×20 [mm] produced by the Ryohin Keikaku Co., Ltd. has been used as the housing 7. Needless to say, this is a mere example. The scope of protection according to the present invention includes modification and/or variation therefrom.

The funnel part 2 is a member for dripping liquid which may contain a sample so as to thoroughly lead the dripped liquid to the filtering material 3. However, if the dripping can be easily carried out, the funnel part 2 may be omitted.

As the funnel part 2, a nozzle part in a shape that is often formed with, for example, a chip of a micropipette, a medicine bottle, or the like may be appropriated.

In this Example, a hole with an about 5 [mm] of diameter is opened through an upper surface of the housing 7, a bottom end of the funnel part 2 is screwed through the opened hole, thereby fixing the funnel part 2 onto the housing 7.

The laminated structure in this Example includes: the filtering material 3; the first water absorption material 4; the second water absorption material 5; and the adjusting member 6, as described below.

In this Example, as the filtering material 3, a circle membrane piece made by punching "Omnipore membrane filter (JCWP)" produced by the Merck "Japan Millipore" by means of a one hall punch (7 [mm] of hole diameter) produced by the Carl Jimuki Co., LTD. is used.

It is preferable that the diameter of the filtering material 3 is about 5 through 7 [mm], and that the pore size of the filtering material 3 is about 1 through 10 [μm].

It is necessary to install the filtering material 3 to fully adhere to the first water absorption material 4 so that the solution 1 does not leak out from the bottom end of funnel part 2, or the like.

In this Example, as the first water absorption material 4, productive filter paper produced by the Toyo Roshi Kaisha, Ltd. (No. 60) is cut into a rectangle of 25.0 [mm]×25.0 [mm], and one sheet of the cut paper is arranged immediately below the filtering material 3.

As the second water absorption material 5, "Whatman glass fiber filter paper rectangle grade GF/D" produced by the GE Healthcare Japan is cut into the rectangle of 25.0 [mm]×25.0 [mm], and two sheets of the cut filter paper are anrranged below the first water absorption material 4.

Furthermore, as the adjusting member 6, a plastic board is laid under the second water absorption material 5. The adjusting member 6 may be omitted in some cases.

In the absorption process of Item 5, the following is carried out:

adding the 50 [μl] of starting material into 600 [μl] of purified water dispensed into a 1.5 [ml] tube;

further adding 40 [μl] of silica-particle suspension thereto;

immediately after that turning the tube over to be mixed (5 [s]);

leaving the tube for 5 [min] at the room temperature; and turning the tube over to be mixed (5 [s]) again.

And then, the followings are further carried out: dripping all amounts of solution containing homogenized nucleic-acid and silica particles onto the funnel part 2 of the filtration device shown in FIG. 2 (e); and performing filtering separation thereon (about 1 through 2 [min]).

After the filtering separation, the composite material of nucleic-acid+silica particles is obtained.

The silica-particle suspension preparation used in Item 5 is prepared by:

adding silica-particles of No. 6 shown in Table 1 to purified water; and preparing the concentration thereof into 1.75 [μg/μl].

The washing process has been performed by adding 600 [μl] of purified water to the obtained composite material of nucleic-acid+silica particles.

After the washing process, the composite material of nucleic-acid+silica particles is picked up by means of tweezers together with the filtering material, immediately after that, adding what has been picked up into 68 [µl] of real-time quantitative PCR reagent to prepare 70 [µl] total amount of real-time quantitative PCR solution including about 2 [µl] of amount of the composite material of nucleic-acid+silica particles with the filtering material; and using what has been prepared for the nucleic-acid amplification reaction.

Similarly, as the positive reference, 70 [µl] total amount of real-time quantitative PCR solution is prepared by:

changing the starting material into 50 [µl] of purified water to carry out Item 5;

after extraction, adding the obtained silica particles and filtering material into the nucleic-acid amplification reaction reagent; and further directly adding 3 [pg] of nucleic-acid sample thereto.

The negative references are composed of: a first negative reference 1 (without the solid-phase carrier) that silica particles have been excluded from Item 5; and a second negative reference 2 (without nucleic-acid sample) that the nucleic-acid sample has been excluded from the positive reference.

TABLE 5

| | Recovery percentage (%) | |
|---|---|---|
| | | Average |
| Item 5 | 37.36 | 26.00 |
| | 34.13 | |
| | 21.32 | |
| | 10.80 | |
| −ref 1 | 2.13 | 1.28 |
| | 0.43 | |
| −ref 2 | 0.99 | 0.52 |
| | 0.05 | |
| +ref | | 100.00 |

Based on the above results, recovery percentages have been calculated as the same as Item 4, and the calculated recovery percentages and an average thereof have been shown in Table 5.

The average of the recovery percentages in Item 5 has reached 26%, which has been higher than what had been expected by the present inventors.

In "Molecular Cloning A LABORATORY MANUAL FOURTH EDITION (Green and Sambrook, Cold Spring Harbor Laboratory Press, Cold Spring Harbor, N.Y., Vol. 1, See, page 4 thereof)," it is considered that 5 through 10% amounts of nucleic-acid remains in a commercial mini-column holding silica substrate for pretreatment even after elution process.

Pleasantly surprised, the result of 26%, which is the average of the recovery percentages in Item 5, is higher than the double of the 5 through 10% amounts, which are the amounts of nucleic-acid that the manual considers to remain and not to be eluted.

In the first negative reference 1, an average of recovery percentages has been low to be 1.28%, which has corresponded to the amounts of nucleic-acid remaining without being eluted there-from and the average of the recovery percentages in Item 5. Due to this, it has been revealed that it has been difficult to obtain an enough amount of nucleic-acid as templates for nucleic-acid amplification reaction without any silica particles.

Referring to the above results, it can be understood that a sufficient amount of nucleic-acid can be retained, because the present method possesses character that the nucleic-acid is hardly eluted even if the target is exposed to solution having a function of eluting the nucleic-acid from the solid-phase carrier, such as the purified water.

It has been shown that the present method can be configured as a form of utilizing, in reaction solution for amplifying nucleic-acid per one test, the retained nucleic-acid for nucleic-acid amplification reaction.

Since the present method does not need the absorption process relying upon the chaotropic effects, various kinds of pretreatment methods can be selected according to a state of a specimen sample.

According to the protocol Y of the BOOM method, about at least 30 minutes is necessary for processing only one sample. Advantageously, according to the present method, the necessary time can be shortened to only about 17 minutes.

In view of the above results, it is apparent that the present method is simple, easy, safe, rapid, and less expensive, and capable of realizing the pretreatment process of genetic screening according to the POCT mode, which cannot be realized due to the conventional methods.

Without almost all the physical and chemical equipment that has been believed to be essential, necessary processes can be performed by means of the filtration device according to the present invention.

The physical and chemical equipment includes: devices used for drying operation (e.g. a heat block); fundamental physical and chemical equipment (e.g. a centrifugal device, a micropipette, or the like.). In other words, the present invention can remove environmental limitation of having the physical and chemical equipment.

The physical and chemical equipment that has been believed to be essential is very expensive, and initial investment costs (e.g. for purchasing the equipment) must be hugely higher than those of POCT kits for immunological examination.

Since using the very expensive equipment can be avoided according to the present invention, costs for extracting nucleic-acid can be reduced remarkably lower.

From another point of view, the present invention can simplify operation procedures by making the washing process easier and allowing to omit the elution process. It is easy even for a person who is not familiar with extraction of nucleic-acid to perform the operation procedures.

Based on the above study, it may be understood that pretreatment methods in the following Embodiments can be carried out.

Needless to say, as repeatedly described above, it is assumed that the condition of the predetermined range is satisfied.

Embodiment 1

FIG. 2 shows processes of a pretreatment method in Embodiment 1 according to the present invention. Embodiment 1 is a basic form of Embodiments following thereafter.

<Extraction Process>

First, as shown in FIG. 2 (a), a sample 12 is added into a tube 10 storing extraction liquid 11 therein.

When the tube is placed still briefly, components (e.g. cell membranes, cell walls, or the like.) covering nucleic-acid of the sample are destroyed by the extraction liquid 11. So, as shown in FIG. 2 (b), the extraction liquid 11 becomes solution containing nucleic-acid that nucleic-acid 13 and contaminant (e.g. broken pieces of cell membranes, or the like.) exist in a mixed mode therein.

<Absorption Process>

Next, as shown in FIG. 2 (c), silica particles 14 are added in the solution containing nucleic-acid within the tube 10 to make the nucleic-acid 13 and the silica particles 14 absorb with each other.

As a result, composite material 15 of the nucleic-acid 13 and the silica particles 14 is formed.

As shown in FIG. 2 (d), this solution is dripped onto the funnel part 2 of the filtration device to be filtered by the filtering material 3, or the like, thereby collecting the composite materials 15 on the filtering material 3 as shown in FIG. 2 (e).

<Washing Process>

As shown in FIG. 2 (f), purified water 16 is dripped onto the composite material 15 having collected on the filtering material 3 to be washed thereby.

As shown in FIG. 2 (g), upon removing the filtering material 3 from the filtration device, as shown in FIG. 2 (h), what has been removed is delivered to the next nucleic-acid-amplification process either as it is or the composite material 15 itself only by having separated the composite material 15 from the filtering material 3.

Embodiment 2

Figure 3:
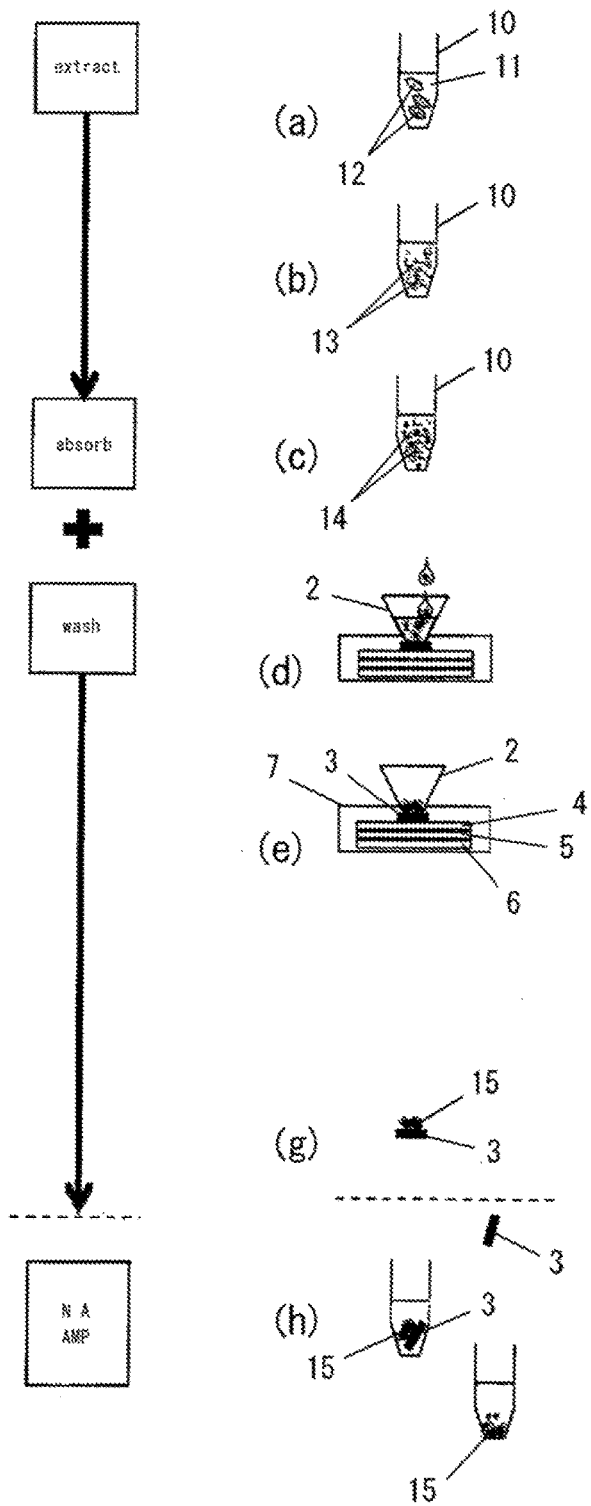
FIG. 3 shows processes of a pretreatment method in Embodiment 2 according to the present invention.

FIG. 3 shows processes of a pretreatment method in Embodiment 2 according to the present invention.

Embodiment 2 is modification of Embodiment 1, and performs both the absorption process and the washing process at the same time.

It is conceivable to use Embodiment 2 for samples including gargle liquid, saliva, lacrima, or the like.

This is because extraction liquid of purified water can be used for these samples, and containing amounts of material inhibiting the nucleic-acid amplification reaction (e.g. protein, lipid, salt, organic solvent, or the like.) are considered to be comparatively less.

<Extraction Process>

The extraction process shown in FIG. 3 (a) and FIG. 3 (b) is the same as that of Embodiment 1.

<Absorption-Process+Washing Process>

Dissimilar to Embodiment 1, washing with the purified water 16 is not performed in the washing process.

Alternatively, as shown in FIG. 3 (d), upon dripping solution onto the funnel part 2 of the filtration device to filter the target by means of the filtering material 3, washing the target with the extraction-liquid 10 itself is also performed.

Points other than the above are the same as those of Embodiment 1.

Embodiment 3

Figure 4:
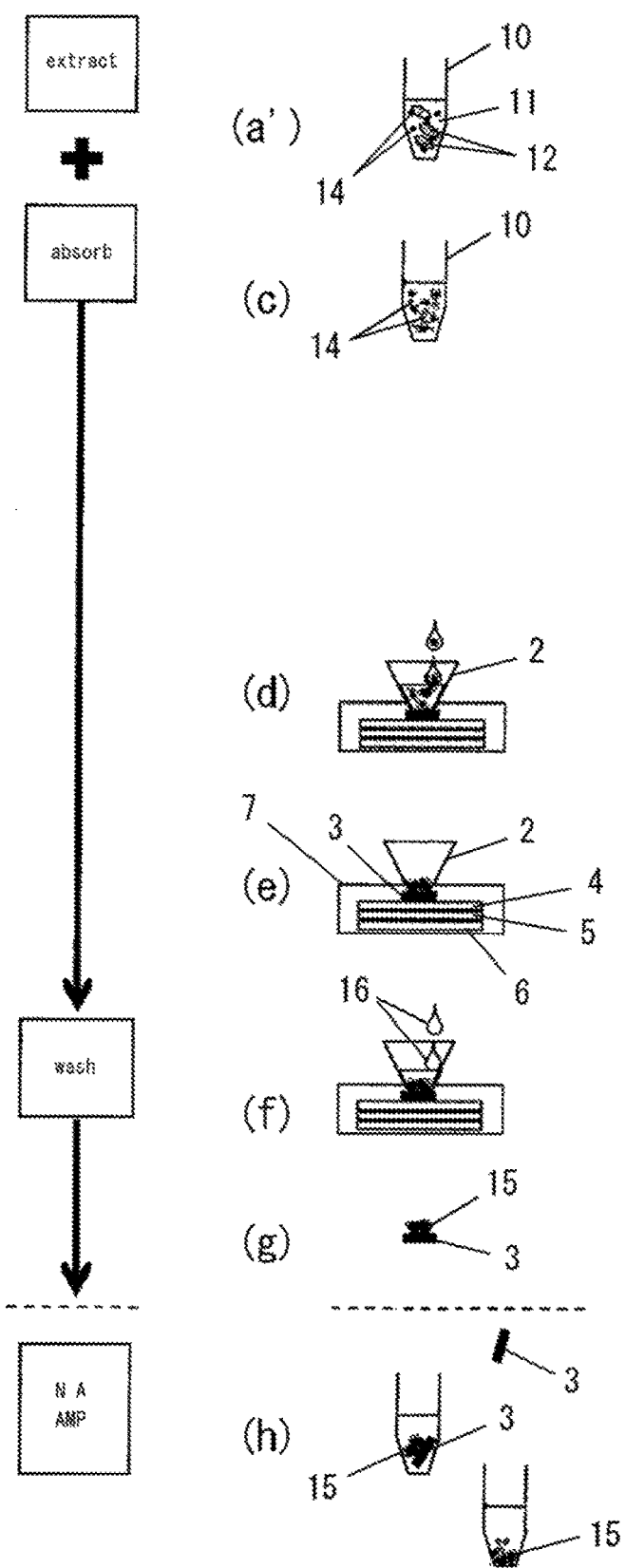
FIG. 4 shows processes of a pretreatment method in Embodiment 3 according to the present invention.

FIG. 4 shows processes of a pretreatment method in Embodiment 3 according to the present invention.

Embodiment 3 is modification of Embodiment 1, and performs both the extraction process and the absorption process at the same time.

Namely, as shown in FIG. 4 (a'), not only the extraction liquid 11 but also the silica particles 14 are beforehand added into the tube 10 such that the predetermined range is satisfied.

The sample 12 is added thereto, the composite material 15 is formed in the tube 10 by not only extracting the nucleic-acid 13 but also making the nucleic-acid 13 and the silica particles 14 absorb with each other.

Points other than the above are the same as those of Embodiment 1.

Embodiment 4

Figure 5:
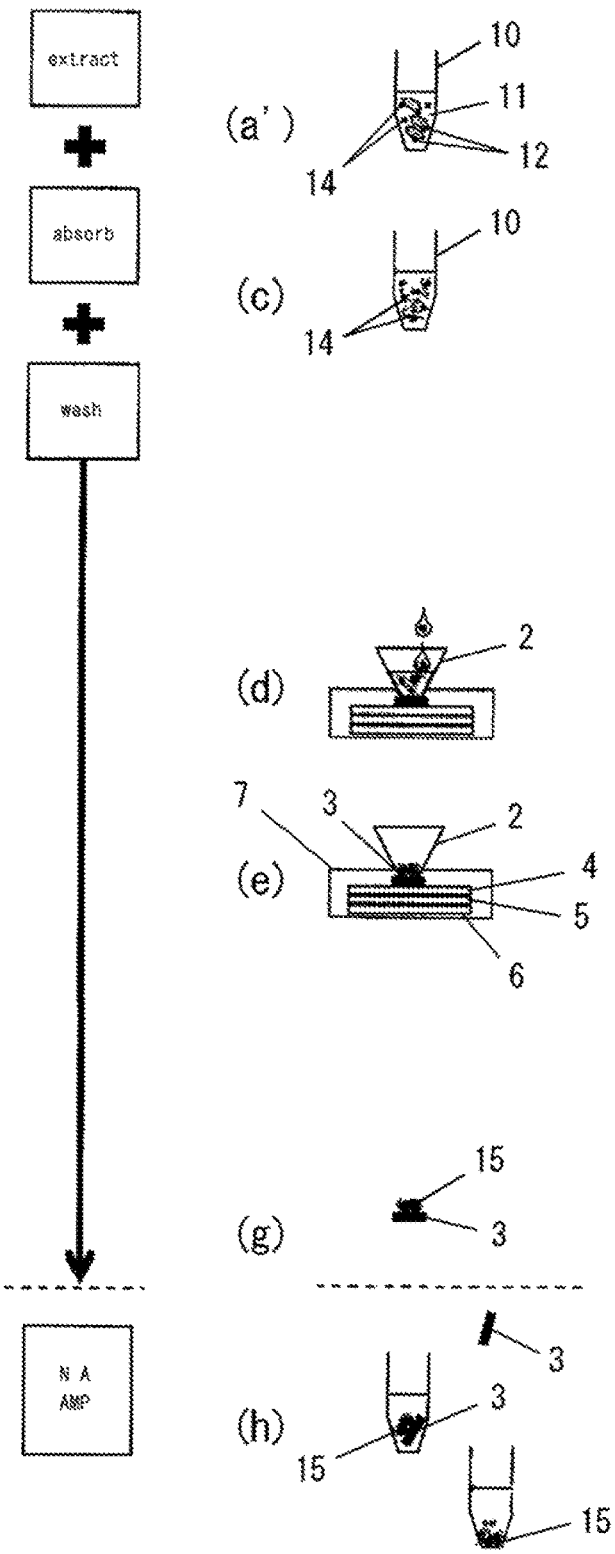
FIG. 5 shows processes of a pretreatment method in Embodiment 4 according to the present invention.

FIG. 5 shows processes of a pretreatment method in Embodiment 4 according to the present invention.

Embodiment 4 is modification of Embodiment 1, and performs the extraction process, the absorption process, and the washing process at the same time.

Embodiment 4 is similar to Embodiment 2 with respect to performing the absorption process and the washing process at the same time. Therefore, it is conceivable to use Embodiment 4 for samples including gargle liquid, saliva, lacrima, or the like.

This is because extraction liquid of purified water can be used for these samples, and containing amounts of material inhibiting the nucleic-acid amplification reaction (e.g. protein, lipid, salt, organic solvent, or the like.) are considered to be comparatively less.

Firstly, as shown in FIG. 5 (a'), not only the extraction liquid 11 but also the silica particles 14 are beforehand added into the tube 10 such that the predetermined range is satisfied.

The sample 12 is added thereto, in the tube 10, not only extraction of the nucleic-acid 13 but also the nucleic-acid 13 and the silica particles 14 which have been extracted are made to adsorb with each other, and then the composite material 15 is formed.

Dissimilar to Embodiment 1, washing with the purified water 16 is not performed in the washing process.

Alternatively, as shown in FIG. 5 (d), upon dripping solution onto the funnel part 2 of the filtration device to filter the target by means of the filtering material 3, washing the target with the extraction-liquid 10 itself is also performed.

Points other than the above are the same as those of Embodiment 1.

Embodiment 5

Figure 6:
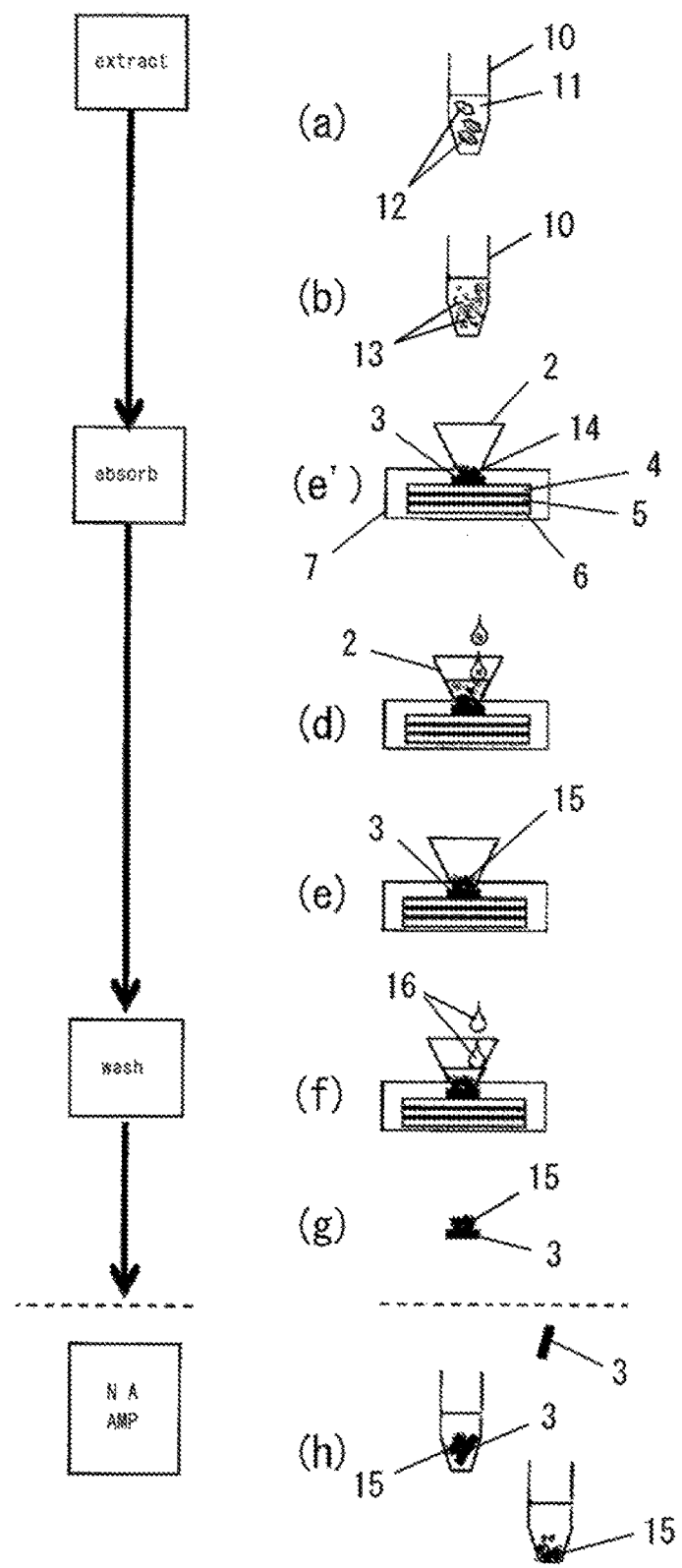
FIG. 6 shows processes of a pretreatment method in Embodiment 5 according to the present invention.

FIG. 6 shows processes of a pretreatment method in Embodiment 5 according to the present invention.

Embodiment 5 can be preferably performed by using a nucleic-acid-extracting kit including the following elements.

The extraction liquid 11 extracts nucleic-acid contained in the sample 12.

The silica particles 14 are disposed on the filtering material 3.

The first water absorption material 4 is arranged to be laid on the filtering material 3, and absorbs water from the extraction liquid dripped onto the filtering material 3. Herein, the particle diameters of the silica particles 14 and the concentration of the silica particles 14 in the reaction solution for amplifying nucleic-acid are set up within the above-mentioned predetermined range such that immediately after the filtering material 3 has been washed the washed filtering material 3 is allowed to be delivered to the nucleic-acid-amplifying process passing through neither a drying process nor an elution process.

<Extraction Process>

First, as shown in FIG. 6 (a), the sample 12 is added in the tube 10 storing the extraction liquid 11 therein.

When the tube is placed still briefly, components (e.g. cell membranes, cell walls, or the like.) covering nucleic-acid of the sample are destroyed by the extraction liquid 11. So, as shown in FIG. 6 (b), the extraction liquid 11 becomes solution containing nucleic-acid that nucleic-acid 13 and contaminant (e.g. broken pieces of cell membranes, or the like.) exist in a mixed mode therein.

<Absorption Process>

In Embodiment 5, dissimilar to Embodiment 1, as shown in FIG. 6 (e'), the silica particles 14 are not added into the solution, but are arranged onto the filtering material 3 of the filtration device.

However, upon dripping the solution containing nucleic-acid in the tube 10 onto the funnel part 2, the nucleic-acid 13 and the silica particles 14 adsorb with each other.

As a result, the composite material 15 of the nucleic-acid 13 and the silica particles 14 is formed.

Points other than the above are the same as those of Embodiment 1.

Embodiment 6

Figure 7:
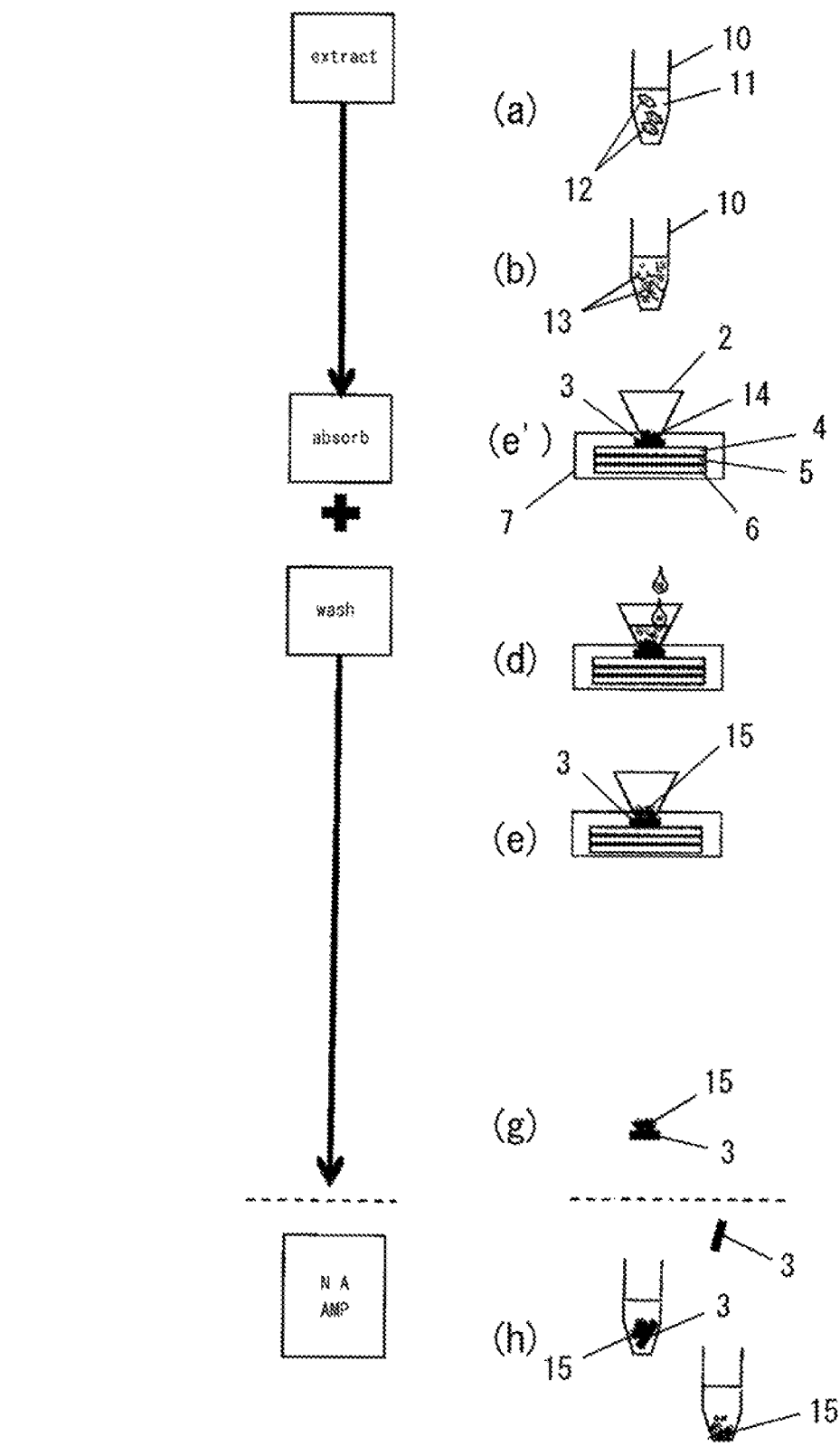
FIG. 7 shows processes of a pretreatment method in Embodiment 6 according to the present invention.

FIG. 7 shows processes of a pretreatment method in Embodiment 6 according to the present invention.

Embodiment 6 modification of Embodiment 5, and performs both the absorption process and the washing process at the same time.

Embodiment 6 is similar to Embodiment 2 with respect to performing the absorption process and the washing process at the same time. Therefore, it is conceivable to use Embodiment 6 for samples including gargle liquid, saliva, lacrima, or the like.

This is because extraction liquid of purified water can be used for these samples, and containing amounts of material inhibiting the nucleic-acid amplification reaction (e.g. protein, lipid, salt, organic solvent, or the like.) are considered to be comparatively less.

Points other than the above are the same as those of Embodiment 5.

What is claimed is:

1. A pretreatment method of extracting nucleic-acid by means of a solid-phase extraction method prior to a nucleic-acid-amplifying process, the pretreatment method comprising:

making a sample, extraction liquid for extracting nucleic-acid contained in the sample, silica particles, and a filtering material contact with each other;

making the filtering material carry composite material of the nucleic-acid and the silica particles thereon; and then delivering the filtering material to a nucleic-acid-amplifying process, the nucleic-acid-amplifying process using a reaction solution for amplifying nucleic-acid, wherein particle diameters of the silica particles and concentration of the silica particles in the reaction solution for amplifying nucleic-acid are set up within a predetermined range;

wherein the predetermined range allows, in advance of the nucleic-acid-amplifying process, omission of both a drying process and an elution process;

wherein the predetermined range is defined as follows:

5% through 38% of the nucleic-acid is recovered from the sample when based on 100% of nucleic-acid contained in the sample;

the concentration of the silica particles is 0.0625 µg/µl through 4 µg/µl;

an average particle diameter of the silica particles is 0.01 µm through 100 µm; and a surface area calculated based on the average particle diameter is $1 \times 10^4$ µm$^2$ through $1 \times 10^8$ µm$^2$; and the pretreatment method further comprises:

a first extraction process of adding the sample to the extraction liquid to extract the nucleic-acid contained in the sample;

a first absorption process of: making the silica particles contact with the extracted nucleic-acid to obtain the composite material of the nucleic-acid and the silica particles; and making the composite material contact with the filtering material;

a first washing process of: washing the composite material and the filtering material with purified water; and delivering the washed composite material and the washed filtering material under a wet condition to the nucleic-acid-amplifying process; and wherein, prior to the delivering the filtering material to the nucleic-acid-amplifying process, the composite material is collected with the filtering material in a manner such that the composite material is on the filtering material.

2. The pretreatment method as defined in claim 1, wherein, prior to the delivering the filtering material to the nucleic-acid-amplifying process, the composite material is separated from the filtering material, and then the separated composite material is delivered to the nucleic-acid-amplifying process.

3. The pretreatment method as defined in claim 1, wherein the first absorption process and the first washing process are performed at the same time.

4. The pretreatment method as defined in claim 1, wherein the first extraction process and the first absorption process are performed at the same time.

5. The pretreatment method as defined in claim 1, wherein the first extraction process, the first absorption process, and the first washing process are performed at the same time.

6. A pretreatment method of extracting nucleic-acid by means of a solid-phase extraction method prior to a nucleic-acid-amplifying process, the pretreatment method comprising:

making a sample, extraction liquid for extracting nucleic-acid contained in the sample, silica particles, and a filtering material contact with each other;

making the filtering material carry composite material of the nucleic-acid and the silica particles thereon; and then delivering the filtering material to a nucleic-acid-amplifying process, the nucleic-acid-amplifying process using a reaction solution for amplifying nucleic-acid, wherein particle diameters of the silica particles and concentration of the silica particles in the reaction solution for amplifying nucleic-acid are set up within a predetermined range;

wherein the predetermined range allows, in advance of the nucleic-acid-amplifying process, omission of both a drying process and an elution process;

wherein the predetermined range is defined as follows:

5% through 38% of the nucleic-acid is recovered from the sample when based on 100% of nucleic-acid contained in the sample;

the concentration of the silica particles is 0.0625 µg/µl through 1 µg/µl;

an average particle diameter of the silica particles is 0.01 µm through 10 µm; and a surface area calculated based on the average particle diameter is $1 \times 10^5$ µm2 through $5 \times 10^7$ µm$^2$; and the pretreatment method further comprises:

a first extraction process of adding the sample to the extraction liquid to extract the nucleic-acid contained in the sample;

a first absorption process of: making the silica particles contact with the extracted nucleic-acid to obtain the composite material of the nucleic-acid and the silica particles; and making the composite material contact with the filtering material;

a first washing process of: washing the composite material and the filtering material with purified water; and delivering the washed composite material and the washed filtering material under a wet condition to the nucleic-acid-amplifying process; and wherein, prior to the delivering the filtering material to the nucleic-acid-amplifying process, the composite material is collected with the filtering material in a manner such that the composite material is on the filtering material.

7. The pretreatment method as defined in claim 6, wherein, prior to the delivering the filtering material to the nucleic-acid-amplifying process, the composite material is separated from the filtering material, and then the separated composite material is delivered to the nucleic-acid-amplifying process.

8. The pretreatment method as defined in claim 6, wherein the first absorption process and the first washing process are performed at the same time.

9. The pretreatment method as defined in claim 6, wherein the first extraction process and the first absorption process are performed at the same time.

10. The pretreatment method as defined in claim 6, wherein the first extraction process, the first absorption process, and the first washing process are performed at the same time.

* * * * *

```
SEQUENCE LISTING

<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Primer for a P1 adhisin gene

<400> SEQUENCE: 1
gccaccctcg ggggcagtca g                                              21

<210> SEQ ID NO 2
<211> LENGTH: 22
<212> TYPE: DNA
<213> ORGANISM: Artificial Sequence
<220> FEATURE:
<223> OTHER INFORMATION: Primer for P1 adhisin gene

<400> SEQUENCE: 2
gagtcgggat tccccgcgga gg                                             22
```